United States Patent
Cui et al.

(10) Patent No.: US 7,586,016 B2
(45) Date of Patent: Sep. 8, 2009

(54) METHOD FOR PRODUCING 1,2-PROPYLENE GLYCOL USING BIO-BASED GLYCEROL

(75) Inventors: Fang Cui, Lanzhou (CN); Jing Chen, Lanzhou (CN); Chungu Xia, Lanzhou (CN); Haixiao Kang, Lanzhou (CN); Xinzhi Zhang, Lanzhou (CN); Jin Tong, Lanzhou (CN); Xuemei Li, Lanzhou (CN)

(73) Assignee: Lanzhou Institute of Chemical Physics, Chinese Academy of Science, Lanzhou (CN)

( * ) Notice: Subject to any disclaimer, the term of this patent is extended or adjusted under 35 U.S.C. 154(b) by 0 days.

(21) Appl. No.: 12/232,982

(22) Filed: Sep. 26, 2008

(65) Prior Publication Data
US 2009/0156866 A1    Jun. 18, 2009

(30) Foreign Application Priority Data
Dec. 13, 2007    (CN) .................. 2007 1 0305964

(51) Int. Cl.
*C07C 29/132* (2006.01)
(52) U.S. Cl. ................................ 568/861
(58) Field of Classification Search ............ 568/861
See application file for complete search history.

(56) References Cited

FOREIGN PATENT DOCUMENTS

| CN | 200610105255.X | 6/2008 |
|---|---|---|
| WO | WO 2007/010299 A1 | 1/2007 |

*Primary Examiner*—Elvis O Price
(74) *Attorney, Agent, or Firm*—Buchanan, Ingersoll & Rooney PC

(57) ABSTRACT

This invention disclosed a method for producing 1,2-propylene glycol from bio-based glycerol. In this method, a $CuO$—$CeO_2$—$SiO_2$ catalyst is filled into a fixed bed reactor, a glycerol solution is flowed into the reactor together with hydrogen gas in a manner of top feeding, and controlling the reaction temperature to be 170~200° C., the reaction pressure to be 1.0~5.0 MPa, so as to realize the production of 1,2-propylene glycol from the hydrogenation of glycerol. The catalyst used in this invention can sustain a high selectivity for the target product and a high conversion for glycerol for 500 hours.

7 Claims, No Drawings

METHOD FOR PRODUCING 1,2-PROPYLENE GLYCOL USING BIO-BASED GLYCEROL

TECHNICAL FIELD

The present invention relates to a method for producing 1,2-propylene glycol by hydrogenating bio-based glycerol.

BACKGROUND ART

Recently, the international demand and production of biodiesel oil (biological diesel oil) are increasing rapidly and the main by-product thereof such as glycerol is also produced abundantly. The key to support the sustainable development for biodiesel oil and the critical task to produce biomass chemicals lie in: researching and developing the bio-based glycerol with an enormous development potential, finding new approaches to produce new products with high additional value from the by-product of biodiesel oil such as glycerol, reducing the cost of biodiesel oil, prolonging the industry chain of biodiesel oil, and increasing the market competitive power of biodiesel oil.

The downstream products of glycerol are various and have attracted the people's universal attention, such as 1,2-propylene glycol prepared from the hydrogenation of glycerol. 1,2-propylene glycol is an important non-toxic chemical primary material applied widely and the main use thereof is being the intermediates of coatings and reinforced plastics during the production of unsaturated polyester resins. 1,2-propylene glycol is the primary material for unsaturated polyester, plasticizer, surfactant, emulsifier and demulsifier. In the industry of polyesters, 1,2-propylene glycol is used for the primary material of polyester polyols, the initiating agent of polyether polyols, the chain extension agent of polyurethane and the like. 1,2-propylene glycol can also be used for antifreezing agent and refrigerant; it has superior sterilizing property and wettability. It can be wildly used for the industries of perfume material, food, cosmetic, medicine, baccy and the like.

There are already many research subjects in China and abroad being carried out and developed on how to realize the preparation of 1,2-propylene glycol from the hydrogenation of glycerol using new process and new technology. Davy Process Technology Co. (WO2007/010299 A1) realized a glycerol conversion of 97~100% and selectivity for 1,2-propylene glycol of 93~97% by using a copper-based catalyst produced by itself.

Lanzhou Institute of Chemical Physics, Chinese Academy of Sciences (Chinese Patent Application No. 200610105255.X) reported a method for preparation of 1,2-propylene glycol from the hydrogenation of glycerol, wherein, a mixed solution system composed of 47.4% of glycerol, 14.3% of water and 40.7% of ethanol was reacted using CuO—$SiO_2$ catalyst under 190° C. and a pressure of 8.0 MPa. The glycerol conversion was up to 96.3% and the selectivity for 1,2-propylene glycol was 99.1% or more. However, this reaction system has the disadvantages of too high reaction pressure and low catalyst stability.

DISCLOSURE OF THE INVENTION

The object of this invention is to provide a method for producing 1,2-propylene glycol using bio-based glycerol.

This invention is realized by the following measures.

The key of the invention lies in the selection of the catalyst and determination of the reaction conditions.

A method for producing 1,2-propylene glycol using bio-based glycerol, characterized in that, in the method, a CuO—$CeO_2$—$SiO_2$ catalyst is filled into a fixed bed reactor, a glycerol solution is flowed into the reactor together with hydrogen gas in a manner of top feeding, and the reaction temperature is controlled to be 170~200° C. and the reaction pressure to be 1.0~5.0 MPa, so as to realize the production of 1,2-propylene glycol by the hydrogenation of glycerol; in the CuO—$CeO_2$—$SiO_2$ catalyst, the mass percent content of CuO is 30~70 wt % and the mass percent content of $CeO_2$ is 3~15 wt %; the solvent in the glycerol solution is selected from a group consisting of methanol, water, or the mixture thereof.

In the method described above, the concentration of the glycerol solution is 40~80 wt %.

In the method described above, the mass space velocity of the glycerol solution is 0.1~2.0/h.

In the method described above, the volume ratio of the hydrogen gas to the glycerol solution (also can be referred to as: hydrogen oil ratio) is 2500~1000:1.

The glycerol described in the invention can be derived from the by-products of the industrial biodiesel oil and can also be the glycerol from other sources.

The preparation method of the catalyst described in the invention comprises:

a, selecting an aqueous solution of copper nitrate, copper chloride, copper sulfate or copper acetate and precipitating it with a NaOH solution of 10 wt %~20 wt % to form a slurry A with a pH of 7~10;

b, mixing the slurry A with a silica sol and aging at a temperature of 30~100° C. for 2~6 hours, then filtering and washing; drying for 12~24 hours at 80~120° C. and baking for 2~6 hours at 300~600° C. to form a catalyst consisting of CuO—$SiO_2$;

c, dipping CuO—$SiO_2$ in a cerium nitrate solution, dring for 2~8 hours at 80~120° C. and baking for 2~6 hours at 300~600° C. to form a catalyst consisting of CuO—$CeO_2$—$SiO_2$;

d, at a temperature of 160~450° C., reducing and activating for 3~18 hours with hydrogen gas or a mixed gas of hydrogen/nitrogen gas, to form the catalyst.

During the process of preparing the catalyst described above, the concentration of the aqueous solution of copper nitrate, copper chloride, copper sulfate or copper acetate is 0.05~1.0 mol/L.

In the step b of preparing the catalyst described above, it is preferable to bake for 3~4 hours at 300~450° C.

This invention has the following advantages:

1, The catalyst can sustain a high selectivity for the target product and a high conversion for glycerol for 500 hours.

2, The glycerol from various sources can be used and the glycerol can be derived from the by-products of the industrial biodiesel oil and can also be the glycerol from other sources.

3, A good reaction can be realized by controlling the reaction pressure to be 1.0~5.0 MPa.

SPECIFIC MODES OF CARRYING OUT THIS INVENTION

Example 1

30 g of crystalline copper nitrate and 200 ml of water were added into a reactor and the solution was stirred at 30° C. Titrating the solution with a 15% sodium hydroxide and the titration was stopped at a pH of 8~9. Slurry A was formed.

Slurry A was mixed with 44 ml of silica sol, raised to 80° C. and aged for 4 hours; filtered; oven-dried for 16 hours at 120° C. and baked for 4 hours at 400° C.

10 g of crystalline cerium nitrate was dissolved with water, and then at a condition of room temperature, the $CuO/SiO_2$ composite oxide was dipped thereto with equal volume and kept for 4 hours. The oxide was oven-dried for 16 hours at 120° C. and baked for 4 hours at 400° C. A CuO(32.0 wt %)-$CeO_2$(8.0 wt %)-$SiO_2$(60.0 wt %) hydrogenation catalyst was obtained. At a temperature of 160~450° C., a catalyst was prepared after the reduction and activation for 3~18 hours with hydrogen gas or the mixed gas of hydrogen gas and nitrogen gas.

Example 2

The catalyst of example 1 was filled into a water/methanol solution of 40% glycerol by a catalyst filling amount of 30 ml. The mixture was reacted at a temperature of 190° C. and a pressure of 4.0 MPa. The glycerol mass space velocity was 0.35/h and the hydrogen oil ratio was 2000:1. After 12 hours, the mixture was sampled and analyzed that the glycerol conversion was 80.0% and the selectivity for 1,2-propylene glycol was 95.7%.

Example 3

The catalyst of example 1 was filled into a water/methanol solution of 40 wt % glycerol by a catalyst filling amount of 200 ml. The mixture was reacted at a temperature of 190° C. and a pressure of 2.0 MPa. The glycerol mass space velocity was 0.25/h and the hydrogen oil ratio was 2000:1. After 12 hours, the mixture was sampled and analyzed that the glycerol conversion was 99.0% and the selectivity for 1,2-propylene glycol was 97.0%.

Example 4

The catalyst of example 1 was filled into a water/methanol solution of 55 wt % glycerol by a catalyst filling amount of 200 ml. The mixture was reacted at a temperature of 190° C. and a pressure of 3.0 MPa. The glycerol mass space velocity was 0.5/h and the hydrogen oil ratio was 2500:1. After 12 hours, the mixture was sampled and analyzed that the glycerol conversion was 92.7% and the selectivity for 1,2-propylene glycol was 97.0%.

Example 5

The catalyst of example 1 was filled into a water/methanol solution of 80 wt % glycerol by a catalyst filling amount of 200 ml. The mixture was reacted at a temperature of 190° C. and a pressure of 4.0 MPa. The glycerol mass space velocity was 0.75/h and the hydrogen oil ratio was 2000:1. After 12 hours, the mixture was sampled and analyzed that the glycerol conversion was 48.1% and the selectivity for 1,2-propylene glycol was 97.0%.

Example 6

The catalyst of example 1 was filled into a water/methanol solution of 40 wt % glycerol by a catalyst filling amount of 6 ml. The mixture was reacted at a temperature of 180° C. and a pressure of 2.0 MPa. The glycerol mass space velocity was 0.25/h and the hydrogen oil ratio was 1600:1. After 12 hours, the mixture was sampled and analyzed that the glycerol conversion was 70.3% and the selectivity for 1,2-propylene glycol was 96.0%.

Example 7

The catalyst of example 1 was filled into a water/methanol solution of 40 wt % glycerol by a catalyst filling amount of 6 ml. The mixture was reacted at a temperature of 170° C. and a pressure of 2.0 MPa. The glycerol mass space velocity was 1.0/h and the hydrogen oil ratio was 1000:1. After 12 hours, the mixture was sampled and analyzed that the glycerol conversion was 50.0% and the selectivity for 1,2-propylene glycol was 97.0%.

Example 8

The catalyst of example 1 was filled into a methanol solution of a glycerol as the by-product of industrial biodiesel oil (40 wt %) by a catalyst filling amount of 30 ml. The mixture was reacted for 500 hours at a temperature of 180° C. and a pressure of 2.0 MPa. The hydrogen oil ratio was 2000:1.

| Time hour | Glycerol conversion(%) | Selectivity for 1, 2-propylene glycol(%) |
| --- | --- | --- |
| 100 | 96.0 | 97.8 |
| 300 | 95.5 | 97.8 |
| 500 | 95.9 | 97.7 |

The invention claimed is:

1. A method for producing 1,2-propylene glycol from bio-based glycerol, characterized in that, in the method, a CuO—$CeO_2$—$SiO_2$ catalyst is filled into a fixed bed reactor, a glycerol solution is flowed into the reactor together with hydrogen gas in a manner of top feeding, and the reaction temperature is controlled to be 170~200° C. and the reaction pressure is controlled to be 1.0~5.0 MPa, thereby the production of 1,2-propylene glycol from the hydrogenation of glycerol is achieved; in the CuO—$CeO_2$—$SiO_2$ catalyst, the mass percent content of CuO is 30~70 wt % and the mass percent content of $CeO_2$ is 3~15 wt %; the solvent in the glycerol solution is selected from a group consisting of methanol, water, or the mixture of methanol and water.

2. The method according to claim 1, characterized in that the concentration of the glycerol solution is 40~80 wt %.

3. The method according to claim 1, characterized in that the mass space velocity of the glycerol solution is 0.1~2.0/h.

4. The method according to claim 1, characterized in that the volume ratio of the hydrogen gas and the glycerol solution is 2500~1000:1.

5. The method according to claim 1, characterized in that the preparation method of the catalyst comprising:
   a, selecting an aqueous solution of copper nitrate, copper chloride, copper sulfate or copper acetate and precipitating it with a NaOH solution of 10 wt %~20 wt % to form a slurry A with a pH of 7~10;
   b, mixing the slurry A with a silica sol and aging for 2~6 hours at a temperature of 30~100° C., then filtering and washing; drying for 12~24 hours at 80~120° C. and baking for 2~6 hours at 300~600° C., whereby a catalyst consisting of CuO—$SiO_2$ being formed;
   c, dipping the CuO—$SiO_2$ in a cerium nitrate solution, drying for 2~8 hours at 80~120° C. and baking for 2~6 hours at 300~600° C. to form a catalyst consisting of CuO—$CeO_2$—$SiO_2$; and
   d, at a temperature of 160~450° C., reducing and activating for 3~18 hours with hydrogen gas or the mixed gas of hydrogen gas and nitrogen gas, to produce the catalyst.

6. The method according to claim 5, characterized in that the concentration of the aqueous solution of copper nitrate, copper chloride, copper sulfate or copper acetate is 0.05~1.0 mol/L.

7. The method according to claim 5, characterized in that in step b in the preparation of the catalyst, the baking is performed for 3~4 hours at 300~450° C.

* * * * *